United States Patent [19]

Cohnen et al.

[11] 4,318,915

[45] Mar. 9, 1982

[54] SUBSTITUTED GUANDINES AND METHODS OF PREPARATION THEREOF

[75] Inventors: Erich Cohnen; Ben Armah; Eva Hofferber, all of Hamburg, Fed. Rep. of Germany

[73] Assignee: Beiersdorf Aktiengesellschaft, Hamburg, Fed. Rep. of Germany

[21] Appl. No.: 167,992

[22] Filed: Jul. 14, 1980

[30] Foreign Application Priority Data

Aug. 4, 1979 [DE] Fed. Rep. of Germany ....... 2931735

[51] Int. Cl.$^3$ ................ A01K 31/165; A01K 31/415; C07C 129/12; C07D 233/48
[52] U.S. Cl. ............................... 424/273 R; 564/170; 564/182; 548/315; 424/324
[58] Field of Search ............... 564/170, 182; 424/320, 424/324, 273 R; 548/315

[56] References Cited

U.S. PATENT DOCUMENTS 3,632,645  1/1972  Bream et al. ................. 564/182
3,634,508  1/1972  Bream et al. ................. 564/182
3,822,262  7/1974  Bream et al. ................. 548/315

Primary Examiner—Natalie Trousof
Assistant Examiner—L. Hendriksen
Attorney, Agent, or Firm—Bierman & Bierman

[57] ABSTRACT

A compound of the formula

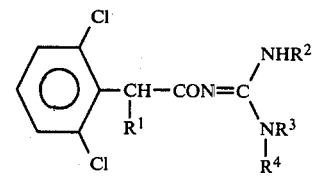

wherein $R^1$ is chlorine, bromine, or methoxy; and $R^2$, $R^3$, and $R^4$ are individually hydrogen or methyl, at least one of $R^2$, $R^3$, and $R^4$ being hydrogen; or $R^2$ and $R^3$ together are an ethylene group and $R^4$ is hydrogen, or a pharmaceutically acceptable acid addition salt thereof. Such compounds are useful as anti-hypertensive agents. Methods of preparation and certain novel intermediates are also disclosed.

11 Claims, No Drawings

SUBSTITUTED GUANDINES AND METHODS OF PREPARATION THEREOF

This application claims the priority of German application No. P 29 31 735.9, filed Aug. 4, 1979.

The present application is directed to certain compounds which have been found uniquely useful as antihypertensive agents. In particular, they are substituted phenyl acetyl guanidines of the formula

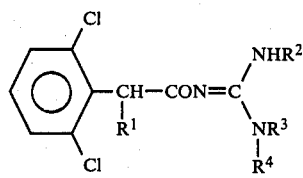

wherein $R^1$ is chlorine, bromine or methoxy, $R^2$, $R^3$, and $R^4$ are individually hydrogen or methyl, and least one of $R^2$, $R^3$ and $R^4$ is hydrogen. Alternatively, $R^2$ and $R^3$ can jointly form an ethylene group, with $R^4$ being hydrogen. The usual physiologically and pharmaceutically acceptable acid addition salts are also part of the present invention.

The end products of the present invention have excellent blood pressure lowering the characteristics and are recommended for treatment of hypertension. The oral dosage in man is approximately 1 to 50 mg per day. These compounds do not cause an initial blood pressure increase as does Guanfacine, a somewhat similar prior art product.

Administration of the present compounds is carried out in the usual way. They can be used as is or in the form of their acceptable acid addition salts. They may be mixed with solid or liquid diluents or carriers and may be administered by any of the usual routes; for example, by mouth or injection. Suitable vehicles include lactose, gelatin, cornstarch, stearic acid, ethanol, propylene glycol, tetrahydrofurfuryl alcohol ether, and water.

The compounds can be prepared by a number of processes. The first process, directed to the form of the invention wherein $R^2$, $R^3$, and $R^4$ are hydrogen, comprises reacting guanidine with a derivative of the formula

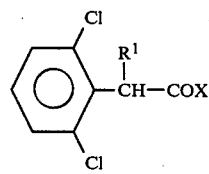

wherein $R^1$ is chlorine, bromine, or methoxy, and x is halogen or alkoxy. The preferred halogens are chlorine and bromine. It is most advantageous to carry out the reaction in the presence of an alcohol such as ethanol, or in a water-acetone mixture. For best results, room temperature or slightly below has been found suitable.

A modification of the foregoing process comprises the reaction of guanadine with a compound of the formula

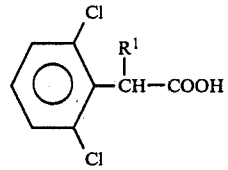

It has been found suitable to carry out this reaction in the presence of a carbodiimide. The preferred carbodiimide is dicyclohexyl carbodiimide and the preferred reaction temperature is 20 to 60 degrees C. The reaction medium can advantageously be a two phase system, such as methylene chloride and water; or an inert solvent such as acetone or dimethoxyethane.

A further process for the production of the compounds of the present invention comprises the reaction of the compound

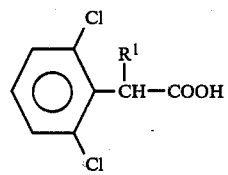

with S-methyl-isothiourea or S-methyl-N-methyl-isothiourea to give an acyliso thiourea of the formula

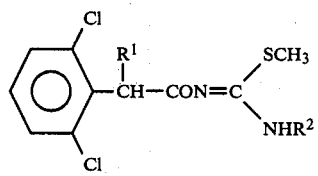

The reaction is preferably carried out in the presence of a carbodiimide such as dicyclohexyl carbodiimide.

This product is then further reacted with either ammonia or an amine of the general formula

In all cases, $R^1$, $R^2$, $R^3$, $R^4$ have the same meanings as previously set forth. The reaction of the thiourea with the phenylacetic acid is preferably carried out at 20 to 60 degrees C., in the presence of an inert solvent such as acetone or dimethoxyethane; or in a two-phase system, such as methylene chloride and water. Of course, it is necessary to select the reactants so that at least one of $R^2$, $R_3$, and $R^4$ is a hydrogen atom.

The reaction with ammonia is preferably carried out with a saturated ethanolic ammonia solution at room temperature. Reaction with the amines is carried out preferably in alcohol solution, most preferably in a mixture of ethanol and isopropanol at slightly elevated temperatures.

A still further process for the production of the present compounds comprises the reaction of S-methyl-isothiourea or S-methyl-N-methyl-isothiourea with a phenylacetic acid derivative of the formula

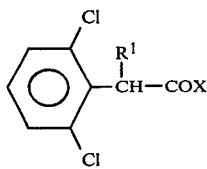

wherein X is halogen or alkoxy. This reaction yields an acyl compound of the formula

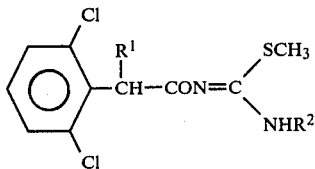

which is further reacted with ammonia or an amine of the formula

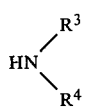

$R^1$, $R^2$, $R^3$, $R^4$ all retain their original meanings as previously set forth. The thioureas react with the phenyl acetic acid compound at room temperature or slightly below, preferably in acetone or an acetone alcohol mixture.

In order to make those compounds of the present invention wherein $R^2$ and $R^3$ together form an ethylene group, the phenylacetic acid derivative of the formula

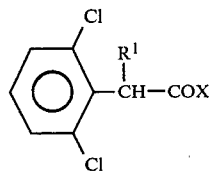

wherein X is halogen, preferably chlorine or bromine, is reacted with 2-amino imidazoline-2. This reaction is conducted with advantage at 0 to 10 degrees C. in dimethoxyethane.

The phenylacetic compound (including both the halide and the corresponding acids) are themselves novel. They can be obtained by the halogenation of 2,6-dichlorophenylacetic acid halides with chlorine or bromine. The reaction occurs advantageously with heating of the reactants to 160 to 180 degrees C. No solvents are required.

The phenylacetyl carboxylic acids, wherein $R^1$ is methoxy, are preferably obtained from the corresponding alpha-bromine compounds by reacting them with sodium methylate.

The customary derivatives of the compounds of the present invention can be made in the usual manner. For example, acid addition salts with hydrochloric, hydrobromic, and sulfuric acids as well as organic acids, such as malonic, maleic, fumaric, and oxalic are all suitable. The list is not intended to be exhaustive, but merely to indicate the breadth and scope of the present invention.

The following examples are intended to further illustrate the nature of the present invention, but are not intended to be limitative.

EXAMPLE 1

[2-(2,6-dichlorophenyl)-2-bromo-acetyl] guanidine

To a solution of 0.072 mols guanidine (from 6.9 g guanidine hydrochloride and 3 g NaOH) in 100 ml water, 20 g (0.06 mols) 2-(2,6-dichlorophenyl)-2-bromo-acetyl-bromide in 50 ml acetone and 2.4 g (0.06 mols) NaOH in 50 ml water at 10 degrees C. are simultaneously added dropwise. After one hour, the organic phase is extracted with methylene chloride, filtered, and further extracted in a counter-current manner with 1 N hydrochloric acid. The acid phase is then adjusted to an alkaline pH and extracted with $CH_2Cl_2$. Subsequent to the evaporation of the methylene chloride, the guanidine base is obtained. It has decomposition point of 155 degrees C. The hydrochloride is prepared in the usual way using ethanolic hydrochloric acid, and is recrystalized from a mixture of acetic acid and ethanol. The decomposition point is 228–229 degrees C.

EXAMPLE 1a

The procedure substantially according to Example 1 was followed to produce [2-(2,6-dichlorphenyl)-2-chloro-acetyl] guanidine. This compound was obtained by an appropriate selection of reactants. The decomposition point of the base is 178–180 degrees C. and that of the hydrochloride is 265 degrees C.

EXAMPLE 1b

By an analogous selection of reactants, the procedure of Example 1 was followed in order to obtain [2-(2,6-dichlorophenyl)-2-methoxy-acetyl] guanidine hydrochloride. The decomposition point is 239–241 degrees C.

EXAMPLE 2

The compound of Example 1b was prepared by stirring 4.0 g (0.016 mols) 2-(2,6-dichlorophenyl)-2-methoxy-acetic acid methyl ester with 0.025 mols guanidine (from 2.4 g guanidine hydrochloride and 0.6 g sodium) in 50 ml ethanol for 2 days at room temperature. After evaporation, the residue is taken up in a water/chloroform mixture, and the chloroform phase is further mixed with ethanolic hydrochloric acid. In this way, the desired hydrochloride salt is obtained. It decomposes at 242 to 243 degrees C.

EXAMPLE 3

The compound of Example 1 was prepared by adding dropwise to 4.3 g (0.015 mols) 2-(2,6-dichlorophenyl)-2-bromo-acetic acid in 50 ml acetone 1.6 g (0.008 mols) dicyclohexyl carbodiimide in 10 ml acetone over a period of 15 minutes. After filtration of the urea, dropwise addition of 1.35 g (0.015 mols) S-methylisothiourea in 25 ml acetone is carried out. Thirty minutes later, the precipitate is suction-filtered, the filtrate evaporated and the residue mixed with acetone and suction-filtered once again. The product of the first stage is S-Methyl-N-[2-(2,6-dichlorophenyl)-2-bromo-acetyl] isothiourea. The decomposition point is 175 degrees C.

In order to obtain the desired product, 3 g of the isothiourea are stirred with 50 ml saturated ammonia solution for 48 hours at room temperature. After the usual work up, the corresponding hydrochloride is obtained. It decomposes at 229–230 degrees C.

EXAMPLE 4

1-Methyl-2-[2-(2,6-dichlorophenyl)-2-bromo-acetyl] guanidine (a) To 7 g S-methylisothiourea in 50 ml of acetone at 10 degrees C., there are added in drops 12 g of 2-(2,6-dichlorophenyl)-2-bromo-acetyl bromide in 30 ml acetone. The mixture is stirred for 30 minutes at 10 degrees C., and the precipitate is suction-filtered. After concentration of the mother liquor, a second fraction of S-methyl-N-[2-(2,6-dichlorophenyl)-2-bromo acetyl] isothiourea is obtained. The decomposition point is 177 degrees.

2 g of the above substance are stirred with 25 ml ethanolic methylamine solution (15%) for 1–2 hours at 30 degrees C. After column chromatography on silica gel, the N-methyl guanidide is obtained as the base, which is then transformed with ethanolic hydrochloric acid into the hydrochloride. The decomposition point is 256–257 degrees C.

(b) In an analogous manner, the compound 1,1-dimethyl-2-[2-(2,6-dichlorophenyl)-2-bromo-acetyl] guanidine is obtained. The melting point is 142–145 degrees C.

EXAMPLE 5

1-methyl-2-methyl-3-[2-(2,6-dichlorophenyl)-2-bromo-acetyl] guanidine 12.0 g (0.035 mole) 2-(2,6-dichlorophenyl)-2-bromo-acetyl bromide in 25 ml acetone are added dropwise to S-methyl-N-methylisothiourea (from 16.4 g S-methyl-N-methyl-isothiouronium iodide and 1.7 g sodium in methanol) in 100 ml acetone. Reaction time: 15 minutes (20 degrees C.). Thereafter the solvent is drawn off, the residue taken up in $CH_2Cl_2$, purified with water free from inorganic components, and recrystallized from ethanol. The melting point is 146–148 degrees C.

By reaction with methylamine in isopropanol (analogous to Example 4) 1-methyl-2-methyl-3-[2-(2,6-dichlorophenyl)-2-bromo-acetyl] guanidine is obtained. The melting point is 127–129 degrees C. The corresponding hydrochloride decomposes at 206–207 degrees C.

Certain of the substances of the foregoing Examples have been tested for their anti-hypertensive activity. Such tests were carred out on genetic (spontaneously) hypertensive) high blood pressure rats (SH Rats) in doses of 0.1 to 10 mg/kg orally or subcutaneously. It was found that the reduction in blood pressure is dose-dependent and, at higher dosages, it can no longer be increased. The maximum reduction was obtained about four hours after the administration of the drug. However, after 24 hours, the blood pressure was still clearly lowered. The initial blood pressure increase, which is observed with the prior art Guanfacine, is not found with the present compounds. The results of the tests are set forth in Table 1.

TABLE 1

Effect on the mean arterial blood pressure in SH rats.

| Example No. | Number of Animals | Dose mg/kg | Antihypertensive action, percent reduction of the initial value | | Initial blood pressure increase in % |
|---|---|---|---|---|---|
| | | | p.o. | s.c. | |
| 1 | 9 | 0.1 | | 21 | |
| | 8 | 1.0 | | 38 | 0 |
| | 8 | 3 | 30 | 45 | |
| | 8 | 10 | 40 | | |
| 4 | 10 | 10 | 38 | | 0 |
| 4b | 9 | 10 | 48 | | 0 |
| | 9 | 1 | 16 | | |
| 5 | 8 | 3 | 36 | | 0 |
| | 9 | 10 | 39 | | |
| Guan-facine* | 7 | 1 | 0 | 14 | |
| | 9 | 3 | 13 | 28 | 15 |
| | 7 | 10 | 28 | | |

*N-amidino-2-(2,6-dichlorophenyl) acetamide hydrochloride

EXAMPLE 6

2-bromo-2-(2,6-dichlorophenyl)-acetyl bromide

To 36.0 g (0.134 mols) 2,6-dichlorophenyl acetyl bromide, are added in drops at 160 degrees C., 21.5 g (0.134 mols) bromine over 3 hours, and the resultant mixture is then stirred for another 2 hours at 170 degrees C. While stirring, 100 ml hexane are added at 90 degrees C., followed by suction-filtering of the bromide after cooling.

Yield 32.7 g. melting point 79–81 degrees C.

EXAMPLE 7

2-chloro-2-(2,6-dichlorophenyl) acetylchloride 69 g (0.31 mols) 2,6-dichlorophenyl acetylchloride are heated to 160 degrees C. and chlorinated by introducing chlorine gas under UV radiation for eight hours.

Yield 50 g. b.p.$_{0.05}$ 86–88 degrees C. b.p.$_{1.2}$ 114–117 degrees C.

EXAMPLE 8

2-bromo-2-(2,6-dichlorophenyl)-acetic acid methyl ester 2-bromo-2-(2,6-dichlorophenyl)-acetic acid methyl ester was produced from 2-bromo-2(2,6 dichlorophenyl)-acetyl bromide and methanol at 20 degrees C. B.p.$_{0.4}$ 130–134 degrees C., M.p. 101–102 degrees C.

EXAMPLE 9

2-(2,6-dichlorophenyl)-2-methoxy-acetic acid and 2-(2,6-dichlorophenyl)-2-methoxy-acetic acid methyl ester 10 g (0.033 mols) 2 bromo-2(2,6-dichlorophenyl)-acetic acid methyl ester (Example 8) are heated with sodium methylate in methanol (1.6 g Na in 100 ml MeOH) in an autoclave for 5 hours at 150 degrees C. After evaporation of the solvent, the residue is taken up in a water-chloroform mixture. By acidification of the aqueous phase, 3.9 g 2-(2,6-dichlorophenyl)-2-methoxy-acetic acid is obtained. It melts at 119–122 degrees C. after recrystallization from diisopropyl ether.

The organic phase contains 4.0 g 2-(2,6-dichlorophenyl)2-methoxy-acetic acid methyl ester having a melting point of 95–96 degrees C.

EXAMPLE 10

2-(2,6-dichlorophenyl)-2-methoxy-acetic acid chloride 3.5 g (0.015 mols) 2-(2,6-dichlorophenyl)-2-methoxy-acetic acid are stirred in 50 ml toluene with 2.0 g (0.017 mols) thionyl chloride for 3 hours at room temperature. After evaporation of the solvent, the desired acid chloride (chromatographically pure) is obtained and it is reacted directly with guanidine as described in Example 1.

EXAMPLE 11

2-(2,6-dichlorophenyl)-2-bromo-acetic acid 6.6 g (0.02 mols) 2-(2,6-dichlorophenyl)-2-bromo-acetyl bromide are stirred with 100 ml 1 N soda lye at 20 degrees C. to form a solution. After acidification and recrystallization from diisopropyl ether, the desired carboxylic acid is obtained. Its melting point is 205-208 degrees C.

EXAMPLE 12

2-[2-(2,6-dichlorophenyl)-2-bromo-acetimino]imidazoline 1.0 g (0.003 mols) 2-(2,6-dichlorophenyl)-2-bromo-acetyl bromide in 10 ml dimethoxyethane is added in drops at 5 degrees C. to a suspension of 2 g 2-aminoimidazoline-2 in 10 ml dimethoxyethane. It is then stirred for 2 hours at 0 degrees C., filtered, and the filtrate evaporated. The residue is taken up in $CH_2Cl_2/H_2O$, and the organic phase is separated and concentrated. The 2-[2-(2,6-dichlorophenyl)-2-bromoacetimino]imidazolidine crystallizes out. Its melting point is 207-208 degrees C.

While only a limited number of specific embodiments of the present invention have been expressly disclosed, it is, nonetheless, to be broadly construed and not to be limited except by the character of the claims appended hereto.

We claim:

1. A compound of the formula

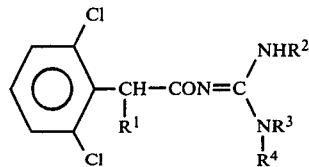

wherein $R^1$ is chlorine, bromine, or methoxy; and $R^2$, $R^3$, and $R^4$ are individually hydrogen or methyl, at least one of $R^2$, $R^3$, and $R^4$ being hydrogen; or $R^2$ and $R^3$ together are an ethylene group and $R^4$ is hydrogen, and pharmaceutically acceptable acid addition salts thereof.

2. A compound according to claim 1 wherein $R^2$, $R^3$, and $R^4$ are hydrogen.

3. A compound according to claim 2 wherein $R^1$ is methoxy.

4. A compound according to claim 1 wherein said formula is 1-methyl-2-[2(2,6-dichlorophenyl)-2-bromo-acetyl]guanidine.

5. A compound according to claim 1 wherein the formula is 1,1-dimethyl-2-[2-(2,6-dichlorophenyl)-2-bromo-acetyl]guanidine.

6. 1-Methyl-2-methyl-3-[2-(2,6-dichlorophenyl)-2-bromo-acetyl]guanidine.

7. A compound according to claim 1 wherein $R^2$ and $R^3$ together form an ethylene group.

8. A pharmaceutical composition for the treatment of hypertension comprising a pharmaceutically acceptable carrier and an amount of a compound of claim 1 or claim 6 sufficient to provide an effective amount of said compound in a warm blooded animal.

9. A composition according to claim 8 wherein said effective amount is 1 to 50 mg/day given orally to human beings.

10. A method of treating hypertension comprising administering an effective amount of a compound of claim 1 or claim 6 to a warm blooded animal.

11. A method according to claim 10 wherein said amount is 1 to 50 mg/day and said animal is a human being.

* * * * *